(12) United States Patent
Choe et al.

(10) Patent No.: US 11,202,658 B2
(45) Date of Patent: Dec. 21, 2021

(54) CONNECTOR FOR SIMULTANEOUSLY FIXING SCREW HEAD AND ROD

(71) Applicants: GANGNEUNG-WONJU NATIONAL UNIVERSITY INDUSTRY ACADEMY COOPERATION GROUP, Gangwon-do (KR); UNIVERSITY OF ULSAN FOUNDATION FOR INDUSTRY COOPERATION, Ulsan (KR)

(72) Inventors: Byung Hak Choe, Gangwon-do (KR); Won Youl Choi, Sejong (KR); Moon Kyu Kim, Gyeonggi-do (KR)

(73) Assignees: GANGNEUNG-WONJU NATIONAL UNIVERSITY INDUSTRY ACADEMY COOPERATION GROUP; UNIVERSITY OF ULSAN FOUNDATION FOR INDUSTRY COOPERATION

( * ) Notice: Subject to any disclaimer, the term of this patent is extended or adjusted under 35 U.S.C. 154(b) by 70 days.

(21) Appl. No.: 16/603,912

(22) PCT Filed: Apr. 10, 2018

(86) PCT No.: PCT/KR2018/004188
§ 371 (c)(1),
(2) Date: Oct. 9, 2019

(87) PCT Pub. No.: WO2018/190610
PCT Pub. Date: Oct. 18, 2018

(65) Prior Publication Data
US 2020/0060730 A1    Feb. 27, 2020

(30) Foreign Application Priority Data

Apr. 12, 2017    (KR) .......................... 10-2017-0047467
Aug. 24, 2017   (KR) .......................... 10-2017-0107433

(51) Int. Cl.
*A61B 17/70*    (2006.01)

(52) U.S. Cl.
CPC ...... *A61B 17/7007* (2013.01); *A61B 17/7032* (2013.01); *A61B 17/7049* (2013.01)

(58) Field of Classification Search
CPC .............. A61B 17/7049; A61B 17/705; A61B 17/7007; A61B 17/7043; A61B 17/7032
See application file for complete search history.

(56) References Cited

U.S. PATENT DOCUMENTS 5,002,542 A      3/1991   Frigg
8,888,819 B2 *  11/2014   Frasier ............... A61B 17/7076
                                                          606/264
(Continued)

FOREIGN PATENT DOCUMENTS

DE    202011107821 U1    4/2012
EP          2455031 A2 *  5/2012 ......... A61B 17/7052
(Continued)

*Primary Examiner* — Julianna N Harvey
*Assistant Examiner* — Holly Joanna Lane
(74) *Attorney, Agent, or Firm* — Stuart H. Mayer; Mayer & Williams PC

(57) ABSTRACT

The present invention relates to a connector for simultaneously fixing a screw head and a rod, wherein the connector can be firmly fixed to a screw head and a rod, which have been surgically inserted, without requiring disassembly of the screw head and the rod, thus minimizing damage to the affected region. The connector may comprise: a connecting block in which a head accommodation hole portion is formed on one side thereof to be able to accommodate at least a portion of a screw head installed in a vertebral body, and a rod accommodation groove portion is formed on the other side thereof to be able to accommodate at least a portion of a rod that extends from the screw head; a connecting rod formed in a shape extending from the (Continued)

connecting block; and a fixing device that fixes the connecting block to the screw head.

7 Claims, 9 Drawing Sheets

(56) References Cited

U.S. PATENT DOCUMENTS

| | | | |
|---|---|---|---|
| 9,770,269 B1* | 9/2017 | Shoshtaev | A61B 17/7055 |
| 10,238,432 B2* | 3/2019 | Carruth | A61B 17/7032 |
| 10,321,939 B2* | 6/2019 | Lee | A61B 17/8645 |
| 2004/0039385 A1 | 2/2004 | Mazda | |
| 2005/0131404 A1* | 6/2005 | Mazda | A61B 17/7035 |
| | | | 606/264 |
| 2008/0177323 A1 | 7/2008 | Null | |
| 2011/0172713 A1* | 7/2011 | Harper | A61B 17/7049 |
| | | | 606/264 |
| 2011/0245872 A1* | 10/2011 | Nilsson | A61B 17/7052 |
| | | | 606/250 |
| 2012/0259369 A1* | 10/2012 | Hammer | A61B 17/7049 |
| | | | 606/251 |
| 2013/0172934 A1 | 7/2013 | Walker | |

FOREIGN PATENT DOCUMENTS

| | | |
|---|---|---|
| EP | 2455031 A2 | 5/2012 |
| EP | 2455031 A3 | 7/2012 |
| EP | 2455031 A8 | 7/2012 |
| KR | 1020090009853 A | 1/2009 |
| KR | 1020090015933 A | 2/2009 |
| KR | 1020090079206 A | 7/2009 |
| KR | 1010008920000 B | 12/2010 |
| KR | 1020120013312 A | 2/2012 |

* cited by examiner

[FIG. 1]
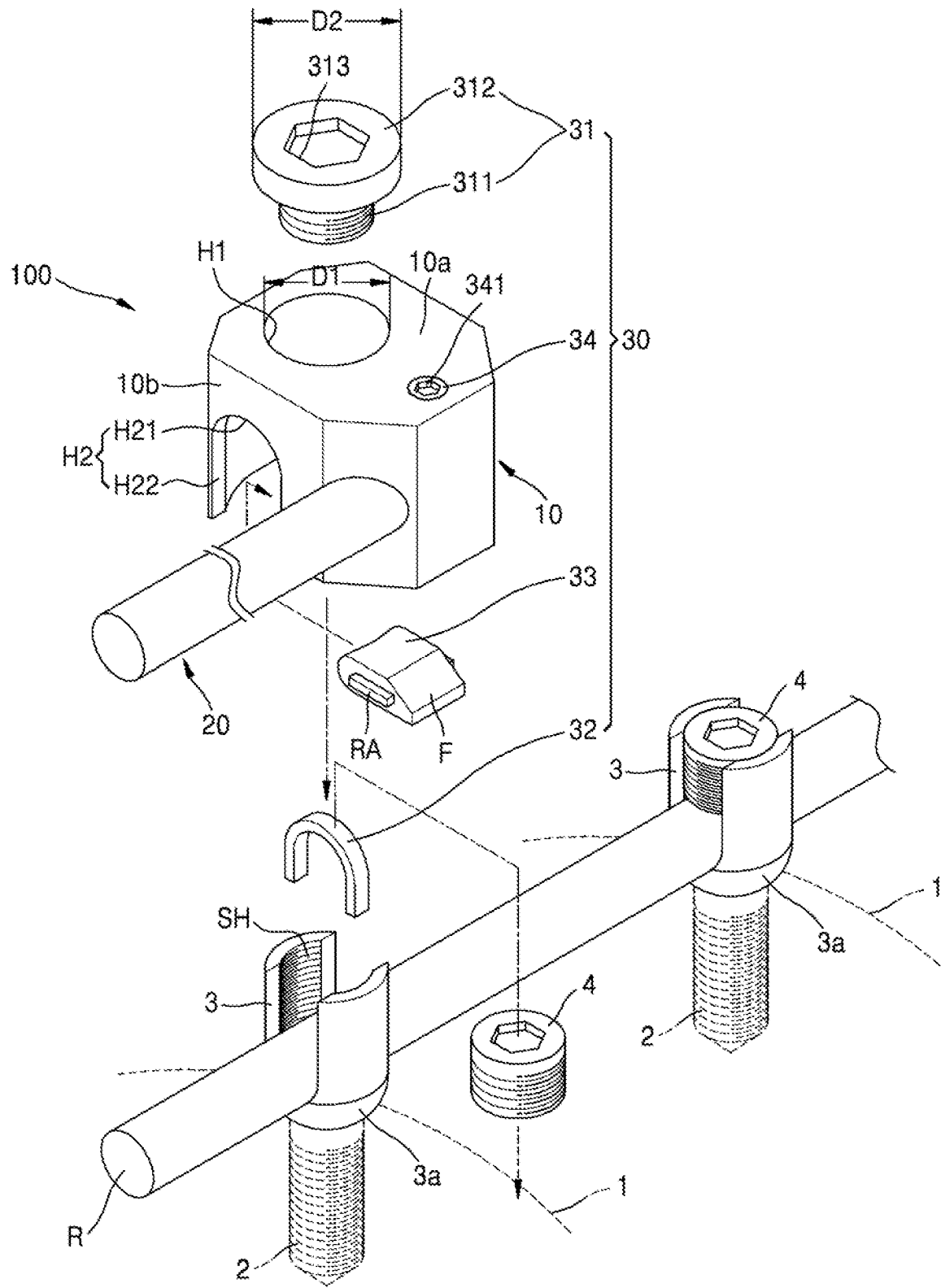

[FIG. 2]
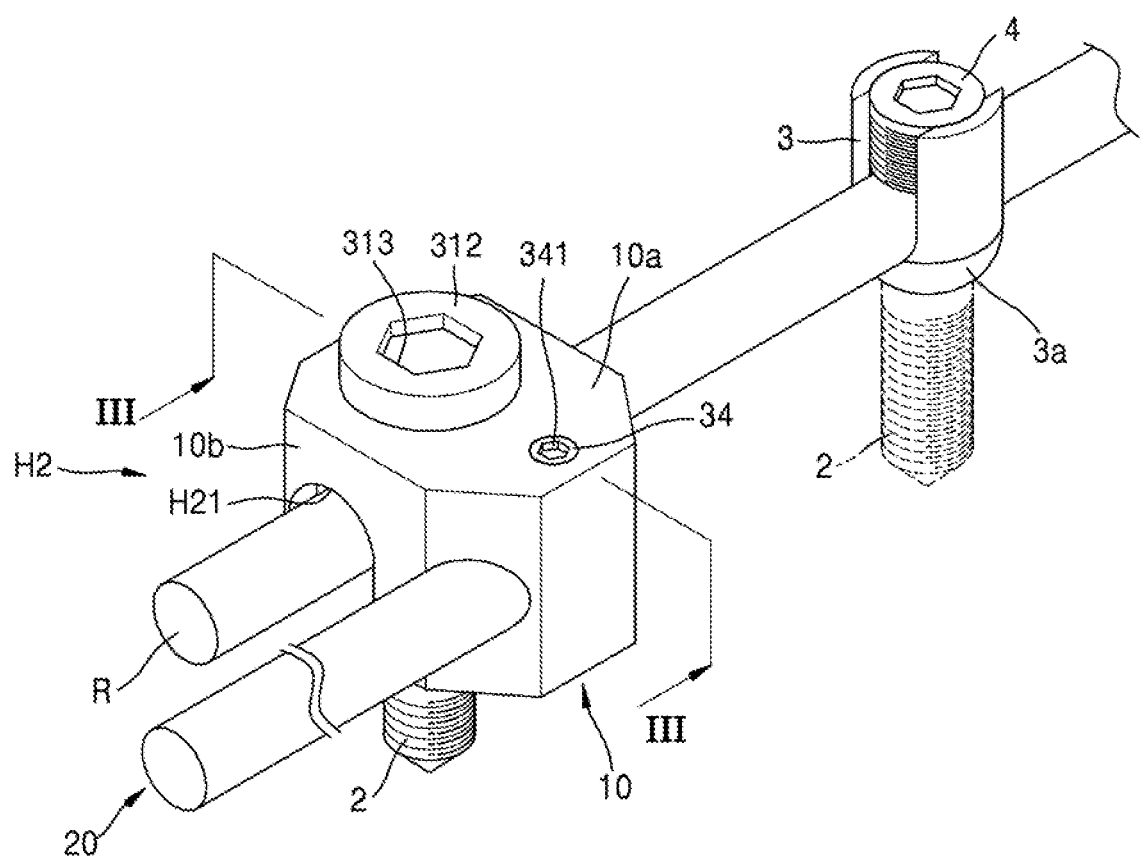

[FIG. 3]
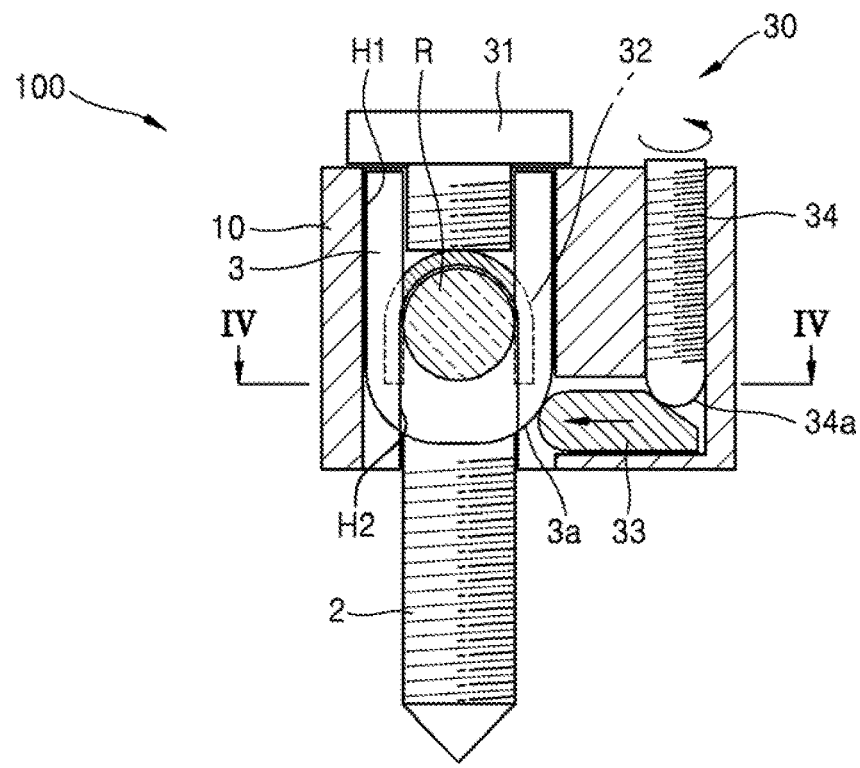
[FIG. 4]
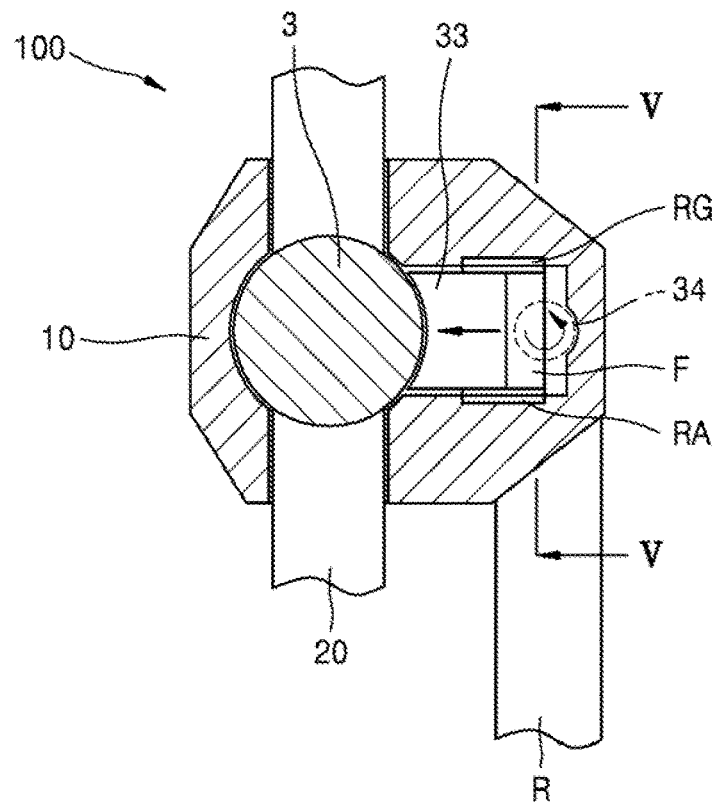

[FIG. 5]
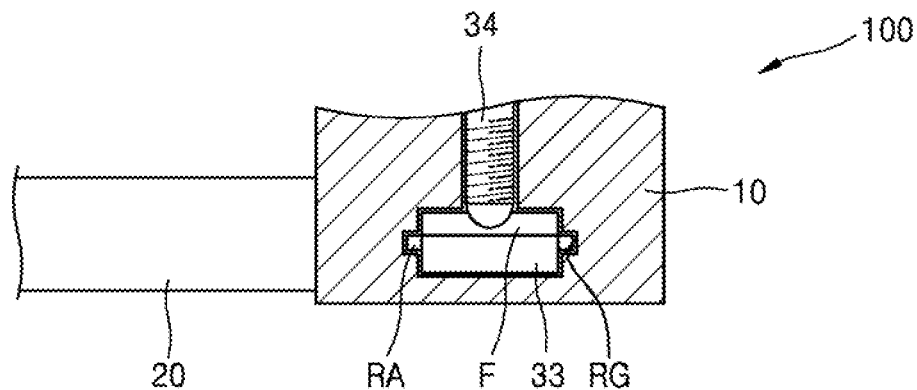
[FIG. 6]
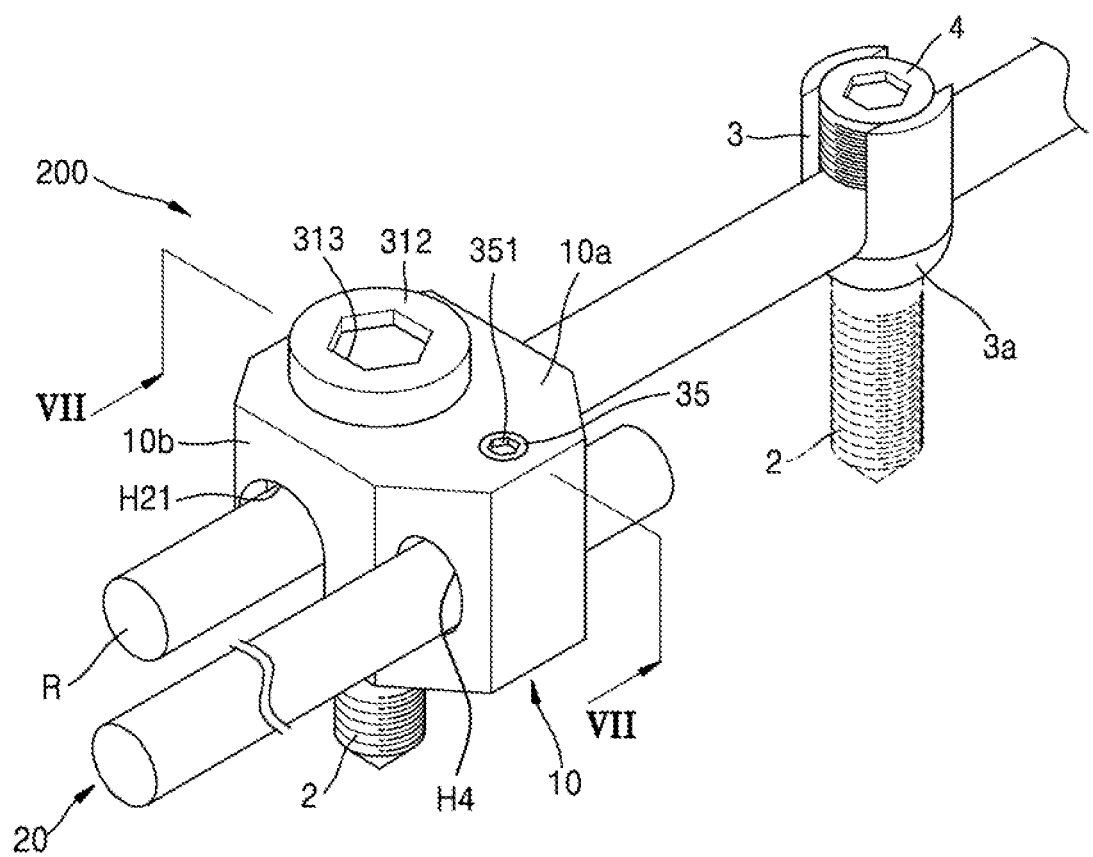

[FIG. 7]
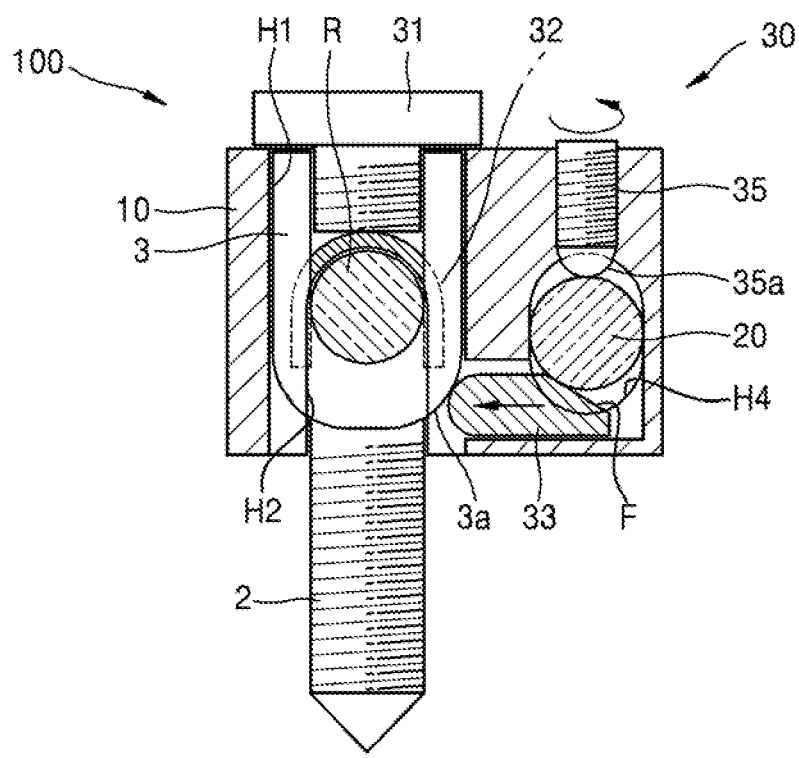

[FIG. 8]
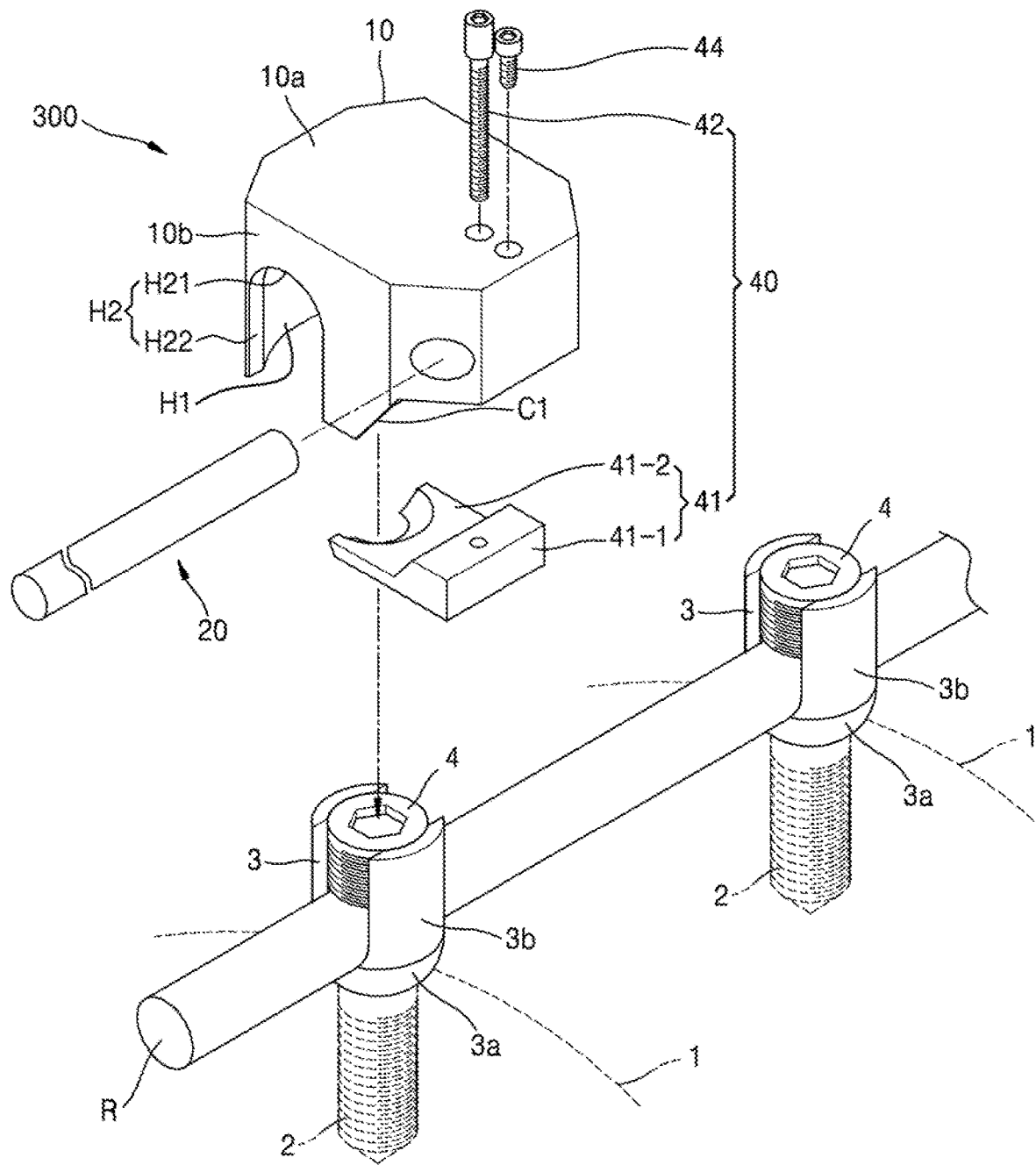

[FIG. 9]
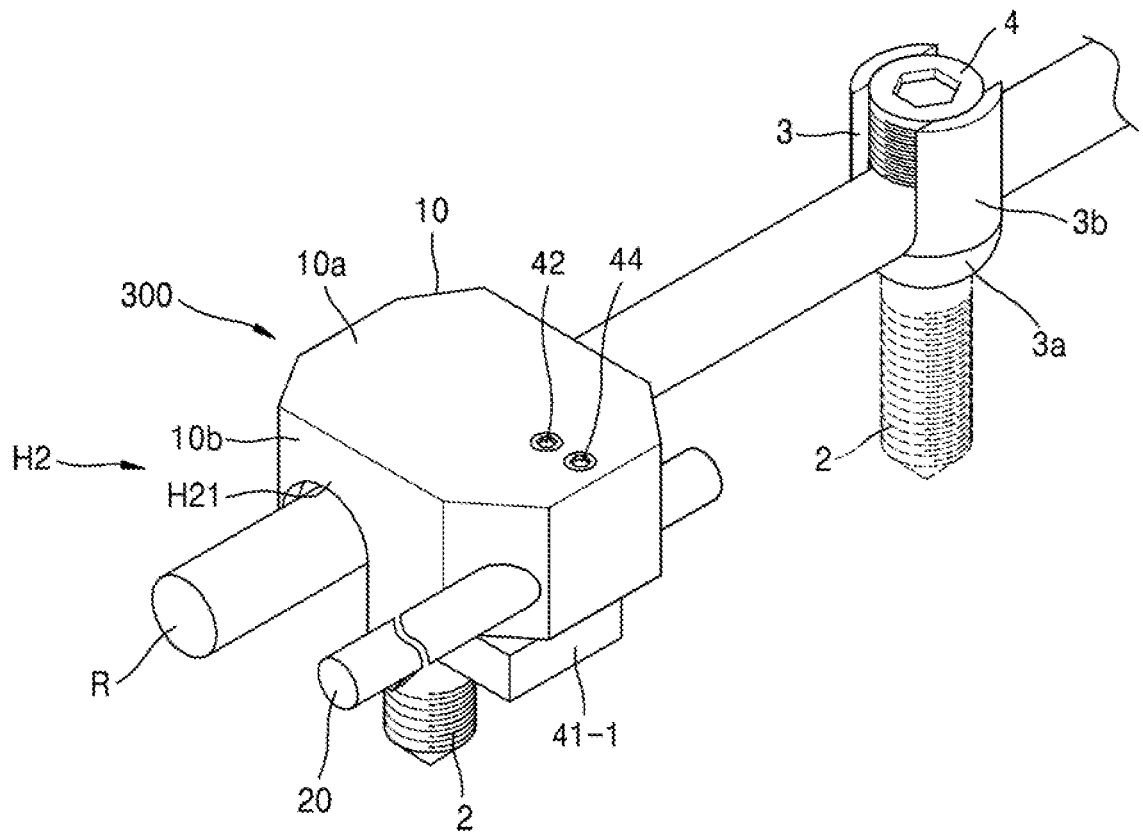
[FIG. 10]
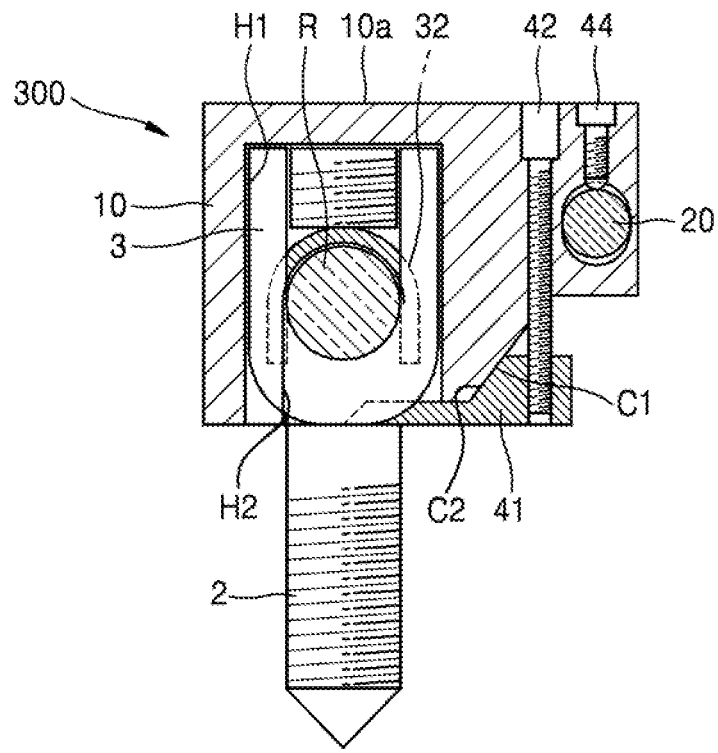

[FIG. 11]
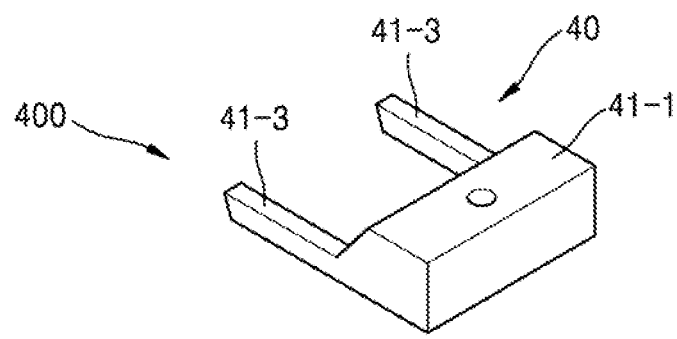
[FIG. 12]
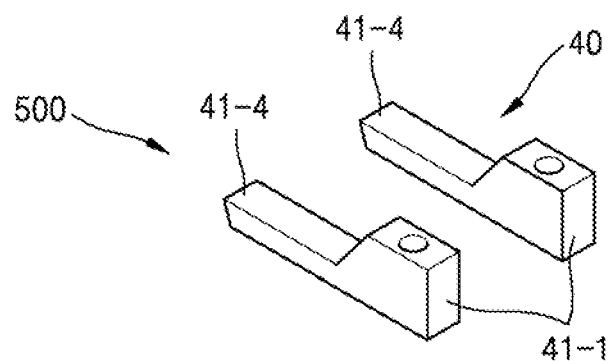

CONNECTOR FOR SIMULTANEOUSLY FIXING SCREW HEAD AND ROD

TECHNICAL FIELD

The present invention relates to a connector for simultaneously fixing a screw head and a rod, and more specifically, to a connector for simultaneously fixing screw head and a rod, wherein additional installation thereof can be easily performed without requiring disassembly of a screw head and a rod, which have been surgically inserted, and the connector can be structurally secured to the screw head and the rod, thus minimizing damage to the affected region.

BACKGROUND ART

In general, the human spine consists of a plurality of vertebral bodies, and intervertebral discs, commonly called discs, are located between adjacent vertebral bodies to support the straightening of vertebral bodies while allowing the spine to move flexibly.

A human being generally has 23 intervertebral discs, which are formed of fibrous cartilage having strong elasticity and expandability and vary in size and thickness depending on the region of the spine. The intervertebral disc and two vertebral bodies form one functional segment of the spine.

Damage or degeneration of the functional segment may develop into stenosis, herniation of intervertebral disc, fracture, or the like, which may compress nerves and may cause back pain and loss of spinal function due to instability.

If a condition is not severe, medication may be administered or a brace or physical therapy may be possible to some extent, but in a severe case where conservative treatment is impossible, spinal fusion is performed.

For spinal fusion, surgery is performed to fix the intervertebral bodies by connecting with screws and rods, wherein adjacent segments of the fixed spine functional segment are structurally subjected to heavy loads during a spine movement of a patient with fixation surgery. Accordingly, a possibility of adjacent joint disease may be increased and a breakage phenomenon of the rod that is located outermost may occur.

In conventional technologies for connecting an additional screw/rod segment related to spinal fusion, one technology is to entirely disassemble an existing segment and then perform a full surgical operation using a closed type connector, and another is to, as disclosed in Korean Patent Registration No. 10-1000892, remove only 2 or 3 previously surgically inserted screws, then connect a rod using an open-type connector in which a portion thereof is open, and re-insert the screws.

Technical Problem

However, as described above, in the case of surgery requiring an additional new segment connection, the two conventional approaches may be accompanied by significant damage to a surgical site where an incision is expanded on the entire or a significant portion of a region around a spine.

In particular, when the closed-type connector is used, a large-scale surgery is required in which a new segment is additionally installed after an existing surgical site is reopened and previously installed screw and rod segments are removed.

Also, when the open-type connector is used, a plurality of open connectors, each with one side open, are used and hence they are physically vulnerable compared to the closed-type, and in order to connect the open connectors, at least two joints of the existing rods must be exposed and implanted bone grafts which are fused between the segments under the rods must be removed again.

That is, the open-type connector also requires a significant incision near the spine and has a drawback in that some of the already fused portion of bone must be removed.

Therefore, due to the conventional problems, there are many difficulties in using the screw connector, such as entirely opening a previous surgical site, and extending the surgical site further downward in a case where an interval for inserting a screw is not sufficient in a place where the connector is located.

The present invention is devised to solve the problems described above, and aims to provide a connector for simultaneously fixing a screw head and a rod, wherein a connecting block capable of simultaneously fixing a screw head and a rod in a double manner can be applied to any screw head products using a conventional method in which a screw head is covered, opening of a previous surgical site can be minimized using the connecting block capable of simultaneously fixing a screw head and a rod firmly in a double manner, and expansion of the surgical site is unnecessary, thus making surgery possible with minimal incision, through which the ease of spinal surgery and a success rate of surgery can be increased and damage to the erector spinae muscles can be prevented, which helps to maintain spine functions of a patient after surgery.

TECHNICAL SOLUTION

A connector for simultaneously fixing a screw head and a rod according to a concept of the present invention to solve the above problems may include a connecting block in which a head accommodation hole portion is formed on one side thereof to be able to accommodate at least a portion of a screw head installed in a vertebral body, and a rod accommodation groove portion is formed on the other side thereof to be able to accommodate at least a portion of a rod that extends from the screw head; a connecting rod formed in a shape extending from the connecting block; and a fixing device which fixes the connecting block to the screw head.

According to the present invention, in the connecting block, the head accommodation hole portion may be formed on an upper surface thereof to penetrate therethrough in a vertical direction so as to surround an outer circumferential surface of the screw head and the rod accommodation groove portion may be formed on a side surface thereof to be connected to the head accommodation hole portion.

According to the present invention, the rod accommodation groove portion may be of an inverted U shape, in which an upper portion thereof is formed in a semicircular shape to correspond to a portion of an outer circumferential surface of the rod and a lower portion thereof is open.

According to the present invention, the fixing device may include an upper fixing screw including a screw portion which is screw-coupled to a screw hole formed in the screw head and a head portion which is connected to the screw portion and has an outer diameter greater than an inner diameter of the head accommodation hole portion.

According to the present invention, the fixing device may further include a half-pipe-shaped protective cover that is formed in a shape corresponding to a portion of the rod to protect the rod from the upper fixing screw and is installed between the upper fixing screw and the rod.

According to the present invention, the fixing device may include a pressing piece which is installed to be able to move forward and backward along a rail groove formed in the connecting block so as to enable a leading end thereof to press a neck portion of the screw head and has an inclined surface formed on a rear end thereof and a tightening screw which is screw-coupled to a tightening screw hole groove portion formed in the connecting block so as to advance the pressing piece by pressing the inclined surface of the pressing piece and has a leading end portion in contact with the inclined surface of the pressing piece.

According to the present invention, the connecting block and the connecting rod may be integrally formed with each other.

According to the present invention, the connecting rod may be detachably inserted into a clearance groove portion formed in the connecting block and the fixing device may include a pressing piece which is installed to be able to move forward and backward along a rail groove formed in the connecting block so as to enable a leading end thereof to press a neck portion of the screw head and has an inclined surface formed on a rear end thereof, and a tightening screw which is screw-coupled to a tightening screw hole portion formed in the connecting block to advance the pressing piece by pressing the inclined surface of the pressing piece and has a leading end portion in contact with the connecting rod.

A connector for simultaneously fixing a screw head and a rod according to a concept of the present invention to solve the above problems may include a connecting rod in which a screw head accommodation groove portion is formed in a lower part thereof in a shape that accommodates an upper portion and a side portion of a head portion of a screw head installed in a vertebral body, and a rod accommodation groove portion is formed on a side thereof to be able to accommodate at least a portion of an existing rod extending from the screw head; a connecting rod which is connected to the connecting block; and a fixing device which fixes the connecting block to the screw head, wherein the fixing device includes a neck pressing member which is formed in a shape corresponding to a neck portion of the screw head inserted into the screw head accommodation groove portion so as to press the neck portion, and a first fastening screw which is installed in the connecting block to fasten the neck pressing member to the connecting block.

According to the present invention, the neck pressing member may have a second inclined surface formed on a portion of an upper surface thereof to correspond to a first inclined surface installed on a lower portion of the connecting block so as to improve close contact with the connecting block.

According to the present invention, the neck pressing member may include a fastening portion on one side thereof to which the first fastening screw is fastened, and a wing portion which is formed to protrude from the fastening portion in a direction of the screw head, is formed in a plane shape to correspond to an circumferential surface of the neck portion of the screw head, and has a rounded concave groove portion in a circular arc shape on a leading end thereof.

According to the present invention, the neck pressing member may include a fastening portion on one side thereof to which the first fastening screw is fastened and at least one arm portion which is formed to protrude from the fastening portion in a direction of the screw head and is formed in a rod shape to be able to press one side surface or the other side surface of the neck portion of the screw head.

According to the present invention, the rod accommodation groove portion may be of an inverted U shape, in which an upper portion thereof is formed in a semicircular shape to correspond to a portion of an outer circumferential surface of the existing rod and a lower portion thereof is open.

According to the present invention, the connecting rod may be detachably inserted into a clearance groove portion formed in the connecting block and the connector may further include a second fastening screw which is installed in the clearance groove portion by penetrating through the connecting block so as to fix the connecting rod to the clearance groove portion.

According to the present invention, the connecting block and the connecting rod may be integrally formed with each other.

Advantageous Effects

According to some embodiments of the present invention, insertion of an additional screw and rod connecting are easily performed with only minimal incision of an affected region, thereby increasing the ease of spinal surgery and the success rate of surgery and preventing damage to erector spinae muscles by repetitive incisions and thus helping to maintain spine functions of the patient after surgery. Also, a portion that catches a rod can resist the force of lateral flexion and thus may be structurally stabilized by being tightly fixed to the rod in a wide friction area unlike an existing structure, and as a result, there is less damage to the affected region and the ease of surgery is greater as compared to all existing connection methods, and fixed stress of a segment is enhanced, so that the success rate of surgery can be greatly improved. However, the scope of the present invention is not limited by these effects.

DESCRIPTION OF DRAWINGS

FIG. 1 is an exploded perspective view of parts constituting a connector for simultaneously fixing a screw head and a rod according to some embodiments of the present invention.

FIG. 2 is a perspective view showing a usage state of the connector of FIG. 1 for simultaneously fixing a screw head and a rod.

FIG. 3 is a cross-sectional view showing cross section of the connector of FIG. 2 for simultaneously fixing a screw head and a rod.

FIG. 4 is a cross-sectional view showing IV-IV cross section of the connector of FIG. 3 for simultaneously fixing a screw head and a rod.

FIG. 5 is a cross-sectional view showing V-V cross section of the connector of FIG. 4 for simultaneously fixing a screw head and a rod.

FIG. 7 is a cross-sectional view showing VII-VII cross-section of the connector of FIG. 6 for simultaneously fixing a screw head and a rod.

FIG. 8 is an exploded perspective view of parts of a connector for simultaneously fixing a screw head and a rod according to some embodiments of the present invention.

FIG. 9 is a perspective view showing a usage state of the connector of FIG. 8 for simultaneously fixing a screw head and a rod.

FIG. 10 is a cross-sectional view showing the connector of FIG. 9 for simultaneously fixing a screw head and a rod.

FIG. 11 is a perspective view showing one example of a neck pressing member of a connector for simultaneously fixing a screw head and a rod according to some other embodiments of the present invention.

FIG. 12 is a perspective view showing another example of a neck pressing member of a connector 500 for simultaneously fixing a screw head and a rod according to still some other embodiments of the present invention.

MODE FOR INVENTION

Figure 6:
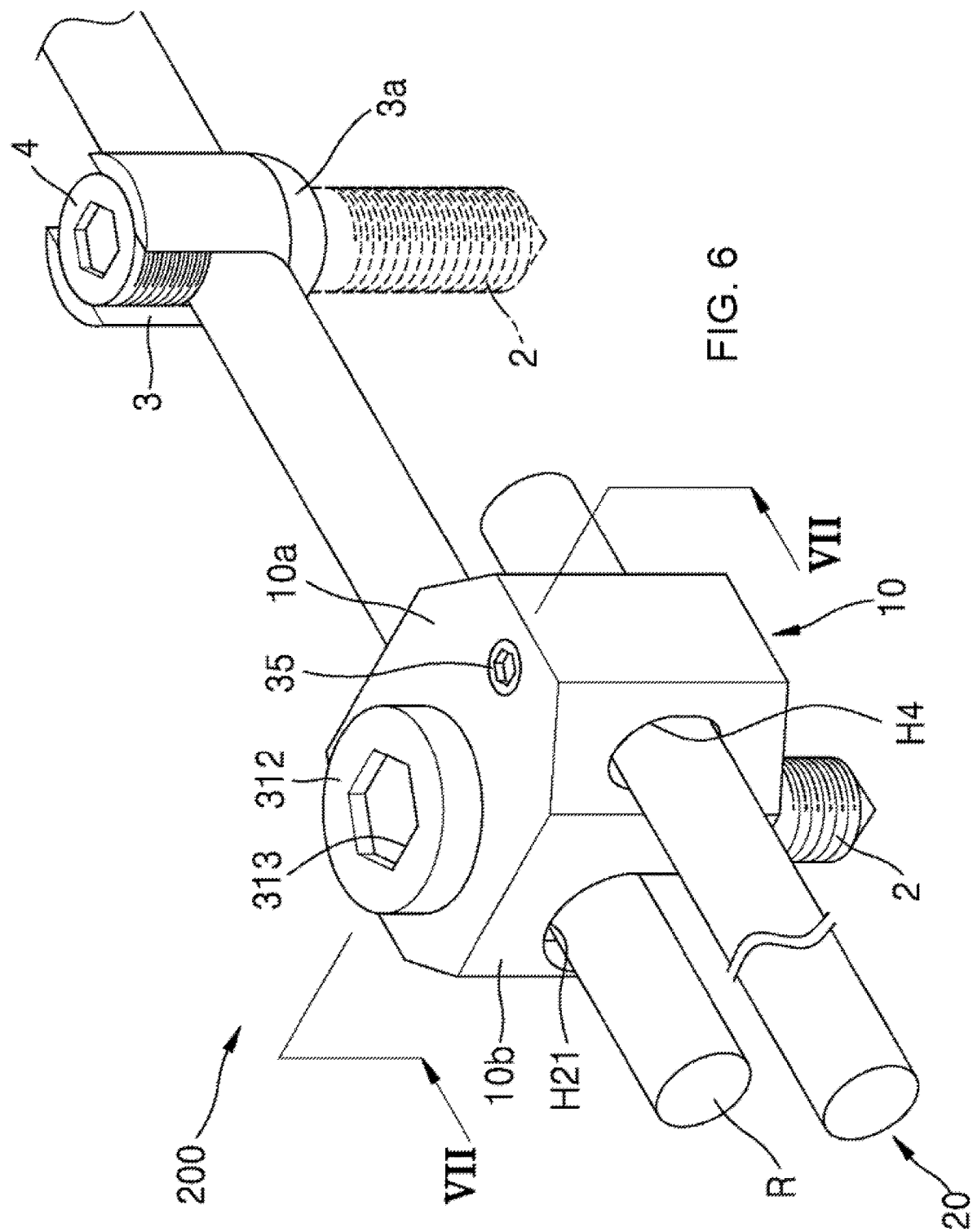
FIG. 6 is a perspective view showing a usage state of a connector for simultaneously fixing a screw head and a rod according to some other embodiments of the present invention.

Hereinafter, the present invention will be described in detail by explaining embodiments of the invention with reference to the attached drawings.

The invention may be embodied in many different forms and should not be construed as being limited to the embodiments set forth herein; rather, these embodiments are provided so that this disclosure will be thorough and complete, and will fully convey the concept of the invention to one of ordinary skill in the art. In the drawings, the sizes of elements may be exaggerated or reduced for convenience of explanation.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, components, and/or groups thereof, but do not preclude the presence or addition of one or more other features, integers, steps, operations, elements, components, and/or groups thereof.

Embodiments of the invention are described herein with reference to drawings that are schematic illustrations of idealized embodiments of the invention. As such, variations from the shapes of the drawings as a result, for example, of manufacturing techniques and/or tolerances, are to be expected. Thus, embodiments of the invention should not be construed as limited to the particular shapes of regions illustrated herein but are to include deviations in shapes that result, for example, from manufacturing.

Hereinafter, a connector for simultaneously fixing a screw head and a rod according to some embodiments of the present invention will be described with reference to accompanying drawings.

FIG. 1 is an exploded perspective view of parts constituting a connector 100 for simultaneously fixing a screw head and a rod according to some embodiments of the present invention. FIG. 2 is a perspective view showing a usage state of the connector 100 of FIG. 1 for simultaneously fixing a screw head and a rod, FIG. 3 is a cross-sectional view showing cross section of the connector 100 of FIG. 2 for simultaneously fixing a screw head and a rod, FIG. 4 is a cross-sectional view showing IV-IV cross section of the connector 100 of FIG. 3 for simultaneously fixing a screw head and a rod, and FIG. 5 is a cross-sectional view showing V-V cross section of the connector 100 of FIG. 4 for simultaneously fixing a screw head and a rod.

First, as shown in FIGS. 1 to 5, the connector 100 for simultaneously fixing a screw head and a rod according to some embodiments of the present invention may largely include a connecting block 10, a connecting rod 20, and a first fixing device 30.

For example, as shown in FIG. 1, the connecting block 10 may be a block structure capable of being fixed to an existing screw head 3 and a rod R, which have been surgically inserted into a vertebral body 1. For example, the connecting block 10 may be a connecting block that is firmly fixed to even one screw head 3 and has sufficient durability and strength to allow the connecting rod 20 to be connected to the existing rod R. Here, the connecting block 10 may be made of various human body-friendly, bioengineered materials, such as titanium, ceramics, and the like.

For example, as shown in FIGS. 1 to 3, the connecting block 10 may be a kind of a box-shaped structure in which a head accommodation hole portion H1 is formed on one side thereof to accommodate at least a portion of the screw head 3 which has been already surgically installed and a rod accommodation groove portion H2 is formed on the other end thereof to accommodate at least a portion of the rod R extending from the already surgically installed screw head 3.

In more detailed example, as shown in FIGS. 1 to 3, in the connecting block 10, the head accommodation hole portion H1 may be formed in a hollow cylindrical shape on an upper surface 10a thereof to penetrate therethrough in a vertical direction so as to surround an outer circumferential surface of the screw head 3 and the rod accommodation groove portion H2 may be formed on a side surface 10b thereof to be connected to the head accommodation hole portion H1.

Here, as shown in FIG. 1, the rod accommodation groove portion H2 may be of an inverted U shape, in which a rod contact portion H21 having a semicircular shape is formed so as to enable an upper portion thereof to correspond to a portion of an outer circumferential surface of the rod R and an opening portion H22 which is open downward is formed.

Therefore, as shown in FIG. 1, since an inner friction surface of the head accommodation hole portion H1 is wide, it is possible to firmly fix the connecting block 10 in directions of front, back, left, and right axes, and at the same time, as the rod R is accommodated in the rod accommodation groove portion H2, the rod accommodation groove portion H2 and the rod R are engaged with each other, so that the connecting block 10 can be more firmly fixed in a double manner on the basis of a rotation axis direction without spinning loosely.

Meanwhile, as shown in FIGS. 1 to 5, the connecting rod 20 may be a cylindrical rod-shaped rod structure formed in a shape extending from the connecting block 10 by a desired length.

In more detailed example, as shown in FIG. 1, the connecting rod 20 may be formed integrally with the connecting block 10.

Therefore, the connecting block 10 and the connecting rod 20 may be formed of the same material and may be prepared in a single shape in various forms, such as cutting, welding, forging, press molding, sintering molding, and the like. However, the connecting block 10 and the connecting rod 20 are not necessarily limited thereto, and may be formed as separate parts.

Meanwhile, as shown in FIGS. 1 to 5, the first fixing device 30 may be a device for fixing the connecting block 10 to the screw head 3 and may include, for example, an upper fixing screw 31, a protective cover 32, a pressing piece 33, and a tightening screw 34.

For example, as shown in FIG. 1, the upper fixing screw 31 may include a screw portion 311 and a head portion 312. The connecting block 10 may be covered over the screw head 3 in a state an existing head cap screw 4 is removed from the screw head 3 where the screw 2 has been already surgically inserted to be screw fixed to the vertebral body 1, and the upper fixing screw 31 may be screw fixed to a screw hole SH formed on the screw head 3.

That is, as shown in FIG. 1, the upper fixing screw 31 may be a kind of cap-shaped screw member consisting of the screw portion 311 which is screw-coupled to the screw hole SH formed on the screw head 3 and the head portion 312 which is connected to the screw portion 311, has an outer diameter D2 greater than an inner diameter D1 of the head accommodation hole portion H1, and includes a wrench groove 313 or a screwdriver groove. In this case, instead of the wrench groove or the screwdriver groove, any shapes in various forms that enable easy rotation, such as a line groove or an angled portion formed on an outer diameter of the head portion 312, may be applied to the head portion 312, without being limited to the drawings.

Thus, an operator who operates spinal fusion may use various tools, such as a wrench, a screwdriver, and the like, to screw fix the upper fixing screw 31 to the existing screw head 3 so that the connection block 10 can be securely fixed to the screw head 3.

Also, for example, the first fixing device 30 may further include the half-pipe-shaped protective cover 32 that is formed in a shape corresponding to a portion of the rod R to protect the rod R from the upper fixing screw 31 and is installed between the upper fixing screw 31 and the rod R. By using the protective cover 32, the rod R may be protected from the upper fixing screw 31 at the time of fixing the upper fixing screw 31 and a pressing area at the time of contacting the rod R may be increased, thereby enabling firmer fixing.

In addition, the first fixing device 30 may further include the pressing piece 33 which has a rail RA formed to move forward and backward along a rail groove RG formed in the connecting block 10 so as to enable a leading end thereof to press a neck portion 3a of the screw head 3 and has an inclined surface F formed on a rear end, and the tightening screw 34 which is screw-coupled to a tightening screw hole portion H3 formed in the connecting block 10 so as to advance the pressing piece 33 by pressing the inclined surface F of the pressing piece 33 and has a leading end portion 34a in contact with the inclined surface F of the pressing piece 33.

Here, a portion of the leading end of the pressing piece 33 in direct contact with the neck portion 3a may have an overall rounded cross-section so as to press the screw head 3 so that the connecting block 10 together with the upper fixing screw 31 can be more firmly fixed to the screw head 3, and said portion may be formed to be concave in shape corresponding to a shape of the neck portion 3a. However, the present invention is not necessarily limited thereto and the leading end may be formed in various shapes that can press the screw head 3.

Further, a head portion of the tightening screw 34 may have a wrench groove 341 or a screwdriver groove formed thereon, so that when an operator advances the tightening screw 34 using various tools, such as a wrench or a screwdriver, the inclined surface of the pressing piece 33 is pressed and upward and downward movement of the tightening screw 34 is converted into forward and backward movement of the pressing piece 33, thereby enabling the leading end of the pressing piece 33 to press the neck portion 3a of the screw head 3, through which the connecting block 10 may be very firmly fixed without being separated from the screw head 3.

In particular, since the connecting block 10 touches the outer circumferential surface of the screw head 3 in a wide contact area to firmly withstand the forces in the front, back, left, and right directions, which are important in the human spine, and at the same time to firmly support the rod R in a double manner, the connecting block 10 can firmly withstand the force in the torsional direction which is very important in the human spine. Therefore, even by fixing the connecting block 10 to only one screw head 3 which has been already surgically inserted, the connecting rod 20 may sufficiently and very firmly withstand forces in all directions.

In addition, a shape of the rail groove RG that guides the pressing piece 33 in forward and backward directions is not limited to the drawings, and a wide variety of grooves and protrusions may be applied.

Hence, by using the connecting block 10 capable of simultaneously fixing the screw head 3 and the rod R firmly in a double manner, it is possible to minimize opening of a previous surgical site and it is unnecessary to expand a surgical site, thus making surgery possible with minimal incision, through which the ease of spinal surgery and a success rate of surgery can be increased and damage to the erector spinae muscles can be prevented, which helps to maintain spine functions of a patient after surgery. This facilitates insertion of an additional screw and rod connecting with only minimal incision of an affected region, thereby increasing the ease of spinal surgery and the success rate of surgery and preventing damage to erector spinae muscles by repetitive incisions and thus helping to maintain spine functions of the patient after surgery. In addition, a portion that catches the rod may resist the force of lateral flexion and thus may be structurally stabilized by being tightly fixed to the rod in a wide friction area unlike an existing structure, and as a result, there is less damage to the affected region and the ease of surgery is greater as compared to all existing connection methods, and fixed stress of a segment is enhanced, so that the success rate of surgery can be greatly improved.

FIG. 6 is a perspective view showing a usage state of a connector 200 for simultaneously fixing a screw head and a rod according to some other embodiments of the present invention, and FIG. 7 is a cross-sectional view showing VII-VII cross-section of the connector 200 of FIG. 6 for simultaneously fixing a screw head and a rod.

As shown in FIGS. 6 and 7, in the connector 200 for simultaneously fixing a screw head and a rod according to some other embodiments of the present invention, a connecting rod 20 may be prepared as a part separate from the connecting block 10, rather than being formed integrally with the connecting block 10, and be detachably inserted into a clearance groove portion H4 formed in the connecting block 10.

Where the connecting rod 20 is prepared as a part separate from the connecting block 10, the first fixing device 30 may include a pressing piece 33 which is installed to be able to move forward and backward along a rail groove RG formed in the connecting block 10 so as to enable a leading end thereof to press a neck portion 3a of the screw head 3 and has an inclined surface F on a rear end thereof, and a tightening screw 35 which is screw-coupled to a tightening screw hole portion H3 formed in the connecting block 10 so as to advance the pressing piece 33 by pressing the inclined surface F of the pressing piece 33 and has a leading end portion 35a in contact with the connecting rod 20.

Therefore, as shown in FIG. 7, when an operator advances the tightening screw 34 using various tools, such as a wrench or a screwdriver, the connecting rod 20 may be pressed by the tightening screw 34 and move downward.

Subsequently, the connecting rod 20 presses the inclined surface of the pressing piece 33, through which the upward and downward movement of the connecting rod 20 is converted into forward and backward movement of the pressing piece 33 and the leading end of the pressing piece 33 may press the neck portion 3a of the screw head 3, thereby allowing the connecting block 10 to be very firmly fixed without being separated from the screw head 3.

FIG. 8 is an exploded perspective view of parts of a connector 300 for simultaneously fixing a screw head and a rod according to some embodiments of the present invention. FIG. 9 is a perspective view showing a usage state of the connector 300 of FIG. 8 for simultaneously fixing a screw head and a rod, and FIG. 10 is a cross-sectional view showing the connector 300 of FIG. 9 for simultaneously fixing a screw head and a rod.

As shown in FIGS. 8 to 10, the connector 300 for simultaneously fixing a screw head and a rod according to some embodiments of the present invention may largely include a connecting block 10, a connecting rod 20, and a second fixing device 40.

The connecting block 10 and the connecting rod 20 are described in detail with reference to FIGS. 1 to 5.

As shown in FIGS. 8 to 12, the second fixing device 40 may be a device for fixing the connecting block 10 to the screw head 3, and may include, for example, a neck pressing member 41 which is formed in a shape corresponding to a neck portion 3a of the screw head 3 inserted into a screw head accommodation groove portion H1 so as to press the neck portion 3a and a first fastening screw 42 which is installed in the connecting block 10 to fasten the neck pressing member 41 to the connecting block 10.

For example, as shown in FIGS. 8 to 10, the neck pressing member 41 may have a second inclined surface C2 formed on a portion of an upper surface thereof to correspond to a first inclined surface C1 installed on a lower portion of the connecting block 10 so as to improve close contact with the connecting block 10.

In more detailed example, the neck pressing member 41 may have a fastening portion 41-1 on one side thereof to which the first fastening screw 42 is fastened and a wing portion 41-2 which is formed to protrude from the fastening portion 41-1 in a direction of the screw head 3, is formed in a plane shape to correspond to an circumferential surface of the neck portion 3a of the screw head 3, and has a rounded concave groove portion G in a circular arc shape on a leading end thereof.

Also, as shown in FIGS. 8 to 10, in the first fastening screw 42, a leading end may penetrate through the fastening portion 41-1 to fasten the neck pressing member 41 to the connecting block 10, a middle portion may vertically penetrate through the connecting block 10, and a rear end may be formed with a screwdriver groove and a wrench groove exposed to the outside such that a user may rotate a screw with a screwdriver or a wrench.

In this case, instead of the screwdriver groove or the wrench groove, any shapes in various forms that enable easy rotation, such as a line groove or an angled portion formed on an outer diameter of the rear end, may be applied without being limited to the drawings.

Thus, the operator who operates spinal fusion may use various tools, such as a wrench or a screwdriver, to fasten the connecting block 10 and the fastening portion 41-1 of the neck pressing member 41 with the first fastening screw 42 so that the wing portion 41-2 can firmly press the neck portion 3a of the screw head 3 and the connecting block 10 can thus be firmly fixed to the screw head 3.

In addition, for example, as shown in FIG. 10, the connector 300 for simultaneously fixing a screw head and a rod according to some embodiments of the present invention may further include a protective cover 32 installed between an existing screw 4 and the rod R. The use of the protective cover 32 may protect the rod R from the existing screw 4 and may increase a pressing area when in contact with the rod R, thereby enabling firmer fixing. However, the present invention is not necessarily limited thereto, such that various parts may be additionally installed.

Also, as shown in FIG. 10, the connecting rod 20 may be detachably inserted into a clearance groove portion H4 formed in the connecting block 10, and a second fastening screw 44 may be installed in the clearance groove portion H4 by penetrating through the connecting block 10 so as to fix the connecting rod 20 to the clearance groove portion H4.

Therefore, the operator may cover the connecting block 10 over the existing screw head 3 and fasten the neck pressing member 41 by using the first fastening screw 42 described above, thereby securing the fastening with the connecting block 10, and thereafter may firmly fix the connecting rod 20 to the connecting block 10 by using the second fastening screw 44.

FIG. 11 is a perspective view showing one example of a neck pressing member 41 of a connector 400 for simultaneously fixing a screw head and a rod according to some other embodiments of the present invention.

As shown in FIG. 11, the neck pressing member 41 of the connector for simultaneously fixing a screw head and a rod according to some other embodiments of the present invention may include a fastening portion 41-1 on one side thereof to which the first fastening screw 42 is fastened and two arm portions 41-3 which protrude from the fastening portion 41-1 in a direction of the screw head 3 and are formed in a rod shape to be able to press each side of the neck portion 3a of the screw head 3.

Thus, the operator who operates spinal fusion may use various tools, such as a wrench or a screwdriver, to fasten the connecting block 10 and the fastening portion 41-1 of the neck pressing member 41 with the first fastening screw 42 so that the arm portions 41-3 can firmly press the neck portion 3a of the screw head 3 and the connecting block 10 can thus be firmly fixed to the screw head 3.

FIG. 12 is a perspective view showing another example of a neck pressing member 41 of a connector 500 for simultaneously fixing a screw head and a rod according to still some other embodiments of the present invention.

As shown in FIG. 12, the neck pressing member 41 of the connector for simultaneously fixing a screw head and a rod according to still some other embodiments of the present invention may include one or more fastening portions 41-1 on one side thereof to which the first fastening screw 42 is fastened and arm portions 41-4 each of which is formed to protrude from each of the fastening portions 41-1 in a direction of the screw head 3 and is in a rod shape to be able to press only one side of the neck portion 3a. In this case, two first fastening screws 42 may be required, one for each fastening portion.

Thus, the operator who operates spinal fusion may use various tools, such as a wrench or a screwdriver, to fasten the connecting block 10 and the fastening portions 41-1 of the neck pressing member 41 with the first fastening screw 42 so that the arm portions 41-4 can firmly press the neck portion 3a of the screw head 3 and the connecting block 10 can thus be firmly fixed to the screw head 3.

However, the neck pressing member 41 is not limited to the drawings, and any members in a wide variety of forms that can be fastened with the first fastening screw 42 to press the neck portion may be applied.

Although the invention has been described and illustrated with reference to specific illustrative embodiments thereof, it is not intended that the invention be limited to those illustrative embodiments. Those skilled in the art will recognize that variations and modifications can be made without departing from the spirit of the invention. It is therefore intended to include within the invention all such variations and modifications that fall within the scope of the appended claims and equivalents thereof.

INDUSTRIAL APPLICABILITY

According to some embodiments of the present invention, application to any screw head products is possible, the ease of spinal surgery and the success rate of surgery are improved, and structural stabilization is achieved such that there is less damage to an affected region and the ease of surgery is greater, as compared to all existing connection methods, and fixed stress of a segment is enhanced, thereby significantly improving the success rate of surgery.

The invention claimed is:

1. A connector for simultaneously fixing a screw head and a rod, the connector comprising:
a connecting block in which a head accommodation hole portion is formed on one side thereof to be able to accommodate at least a portion of a screw head configured for installation in a vertebral body, and a rod accommodation groove portion is formed on the other side thereof to be able to accommodate at least a portion of a rod that extends from the screw head;
a connecting rod formed in a shape extending from the connecting block; and
a fixing device which fixes the connecting block to the screw head,
wherein the fixing device includes a pressing piece which is installed to be able to move forward and backward along a rail groove formed in the connecting block so as to enable a leading end thereof to press a neck portion of the screw head and has an inclined surface formed on a rear end thereof and a tightening screw which is screw-coupled to a tightening screw hole groove portion formed in the connecting block so as to advance the pressing piece by pressing the inclined surface of the pressing piece and has a leading end portion in contact with the inclined surface of the pressing piece.

2. The connector of claim 1, wherein in the connecting block, the head accommodation hole portion is formed on an upper surface thereof to penetrate therethrough in a vertical direction so as to surround an outer circumferential surface of the screw head and the rod accommodation groove portion is formed on a side surface thereof to be connected to the head accommodation hole portion.

3. The connector of claim 2, wherein the rod accommodation groove portion is of an inverted U shape, in which an upper portion thereof is formed in a semicircular shape to correspond to a portion of an outer circumferential surface of the rod and a lower portion thereof is open.

4. The connector of claim 1, wherein the fixing device includes an upper fixing screw including a screw portion which is screw-coupled to a screw hole formed in the screw head and a head portion which is connected to the screw portion and has an outer diameter greater than an inner diameter of the head accommodation hole portion.

5. The connector of claim 4, wherein the fixing device further includes a half-pipe-shaped protective cover that is formed in a shape corresponding to a portion of the rod to protect the rod from the upper fixing screw and is installed between the upper fixing screw and the rod.

6. The connector of claim 1, wherein the connecting block and the connecting rod are integrally formed with each other.

7. A connector for simultaneously fixing a screw head and a rod, the connector comprising:
a connecting block in which a head accommodation hole portion is formed on one side thereof to be able to accommodate at least a portion of a screw head configured for installation in a vertebral body, and a rod accommodation groove portion is formed on the other side thereof to be able to accommodate at least a portion of a rod that extends from the screw head;
a connecting rod formed in a shape extending from the connecting block; and
a fixing device which fixes the connecting block to the screw head, wherein the connecting rod is detachably inserted into a clearance groove portion formed in the connecting block and the fixing device includes a pressing piece which is installed to be able to move forward and backward along a rail groove formed in the connecting block so as to enable a leading end thereof to press a neck portion of the screw head and has an inclined surface formed on a rear end thereof and a tightening screw which is screw-coupled to a tightening screw hole portion formed in the connecting block to advance the pressing piece by pressing the inclined surface of the pressing piece and has a leading end portion in contact with the connecting rod.

* * * * *